(12) United States Patent
Yu et al.

(10) Patent No.: US 10,018,583 B2
(45) Date of Patent: Jul. 10, 2018

(54) CARBON MATERIAL SUPPORTED HOLLOW METAL OXIDE NANOPARTICLES, METHODS AND APPLICATIONS

(71) Applicants: CORNELL UNIVERSITY, Ithaca, NY (US); HUAZHONG UNIVERSITY OF SCIENCE AND TECHNOLOGY, Wuhan, Hubei (CN)

(72) Inventors: Yingchao Yu, Ithaca, NY (US); Héctor D. Abruña, Ithaca, NY (US); Deli Wang, Hubei (CN); Weidong Zhou, Ithaca, NY (US); Liu Hongfang, Hubei (CN); Qin Shuang, Hubei (CN)

(73) Assignees: Cornell University, Ithaca, NY (US); Huazhong University of Science and Technology, Wuhan (CN)

( * ) Notice: Subject to any disclaimer, the term of this patent is extended or adjusted under 35 U.S.C. 154(b) by 0 days.

(21) Appl. No.: 14/778,129

(22) PCT Filed: Mar. 21, 2014

(86) PCT No.: PCT/US2014/031430
§ 371 (c)(1),
(2) Date: Sep. 18, 2015

(87) PCT Pub. No.: WO2014/153503
PCT Pub. Date: Sep. 25, 2014

(65) Prior Publication Data
US 2016/0131609 A1   May 12, 2016

Related U.S. Application Data

(60) Provisional application No. 61/816,436, filed on Apr. 26, 2013.

(30) Foreign Application Priority Data

Mar. 21, 2013   (CN) .................. 103219510

(51) Int. Cl.
G01N 27/30   (2006.01)
H01M 4/36   (2006.01)
(Continued)

(52) U.S. Cl.
CPC ........... *G01N 27/308* (2013.01); *H01G 11/24* (2013.01); *H01G 11/30* (2013.01); *H01G 11/32* (2013.01);
(Continued)

(58) Field of Classification Search
CPC ........ H01G 11/24; H01G 11/30; H01G 11/32; H01G 11/46; H01M 4/366; H01M 4/0416;
(Continued)

(56) References Cited

U.S. PATENT DOCUMENTS

| 6,210,800 | B1 * | 4/2001 | Nesper ................. B01J 35/02 |
| | | | 423/492 |
| 2013/0215513 | A1 * | 8/2013 | Liang ................... G02B 1/11 |
| | | | 359/601 |

FOREIGN PATENT DOCUMENTS

| CN | 102208641 | 10/2011 |
| CN | 102646817 | 8/2012 |
| KR | 20080051954 A | * 6/2008 |

OTHER PUBLICATIONS

Definition of "impregnate," accessed online at https://www.merriam-webster.com/dictionary/impregnate on Mar. 19, 2017.*
(Continued)

Primary Examiner — Daniel C McCracken
(74) Attorney, Agent, or Firm — Hodgson Russ LLP

(57) ABSTRACT

A method for preparing a material composition comprising a hollow transition metal oxide nanoparticle supported upon a carbon material support includes a solution impregnation process step, followed by a thermal reduction process step (Continued)

and finally a thermal oxidation process step. The material composition, an electrode and an electrical component such as but not limited to a battery are all predicated at least in-part upon the material composition prepared in accord with the foregoing method. The foregoing material composition, electrode, battery and method may ultimately provide a LIB with enhanced performance.

1 Claim, 8 Drawing Sheets

(51) Int. Cl.
| | |
|---|---|
| H01M 4/525 | (2010.01) |
| H01G 11/24 | (2013.01) |
| H01M 4/583 | (2010.01) |
| H01M 4/04 | (2006.01) |
| H01G 11/46 | (2013.01) |
| H01G 11/32 | (2013.01) |
| H01M 10/0525 | (2010.01) |
| H01M 4/48 | (2010.01) |
| H01M 4/485 | (2010.01) |
| H01M 4/587 | (2010.01) |
| H01M 4/505 | (2010.01) |
| H01M 4/62 | (2006.01) |
| H01G 11/30 | (2013.01) |

(52) U.S. Cl.
CPC .......... *H01G 11/46* (2013.01); *H01M 4/0416* (2013.01); *H01M 4/366* (2013.01); *H01M 4/48* (2013.01); *H01M 4/485* (2013.01); *H01M 4/505* (2013.01); *H01M 4/525* (2013.01); *H01M 4/583* (2013.01); *H01M 4/587* (2013.01); *H01M 4/625* (2013.01); *H01M 10/0525* (2013.01); *H01M 4/362* (2013.01); *Y02E 60/13* (2013.01)

(58) Field of Classification Search
CPC ........ H01M 4/48; H01M 4/485; H01M 4/505; H01M 4/525; H01M 4/583; H01M 4/587; H01M 4/625; H01M 10/0525; H01M 4/362; Y02P 70/54; Y02E 60/13
See application file for complete search history.

(56) References Cited

OTHER PUBLICATIONS

Scientific Background on the Nobel Prize in Physics 2010 Graphene compiled by the Class for Physics of the Royal Swedish Academy of Sciences, Oct. 5, 2010.*
Wu, et al., Graphene Anchored with Co3O4 Nanoparticles as Anode of Lithium Ion Batteries with Enhanced Reversible Capacity and Cyclic Performance, ACS Nano 2010; 4(6): 3187-3194, with Supporting Information.*
Wang, et al., Enhanced oxygen reduction at Pd catalytic nanoparticles dispersed onto heteropolytungstate-assembled poly(diallyldimethylammonium)-functionalized carbon nanotubes, Phys. Chem. Chem. Phys. 2011; 13: 4400-4410.*
Wang, et al., Facile Synthesis of Carbon-S—pported Pd—Co Core-Shell Nanoparticles as Oxygen Reduction Electrocatalysts and Their Enhanced Activity and Stability with Monolayer Pt Decoration, Chem. Mater. 2012; 24(12): 2274-2281.*
Wang, et al., Structurally ordered intermetallic platinum-cobalt core-shell nanoparticles with enhanced activity and stability as oxygen reduction electrocatalysts, Nature Nanomaterials 2013; 12: 81-87.*
Hu, et al., Fabrication Based on the Kirkendall Effect of Co3O4 Porous Nanocages with Extraordinarily High Capacity for Lithium Storage, Chem. Eur. J. 2012; 18: 8971-8977, with Supporting Information.*
Lin, et al., The mechanism of reduction of cobalt by hydrogen, Materials Chemistry and Physics 2004; 85: 171-175.*
Wang, et al., Template-Free Synthesis of Hollow-Structured Co3O4 Nanoparticles as High-Performance Anodes for Lithium-Ion Batteries, ACS Nano 2015; 9(2): 1775-1781.*
International Search Report and Written Opinion Form PCT/ISA/220, International Application No. PCT/US2014/031430, pp. 1-13, International Filing Date Mar. 21, 2014.
Ahmed, Jalal et al., "Carbon Supported Cobalt Oxide Nanoparticles-Iron Phtha Locyanine as Alternative Cathode Catalyst for Oxygen Reduction in Microbial Fuel Cells", Journal of Power Sources, 208 (2012), pp. 170-175.
Ha, Don-Hyung et al., "Binder-Free and Carbon-Free Nanoparticle Batteries: A Method for Nanoparticle Electrodes Without Polymeric Binders or Carbon Black" , Nano Letters 2012, 12, pp. 5122-5130.
Yang, Zichao et al., "An In Situ Method of Creating Metal Oxide-Carbon Compo Sites and Their Application As.Anode Materials for Lithium-Ion Batteries", J. Mater. Chem. 2011, 21, pp. 11092-11097.
Baron, Miriam et al., "Spontaneous Format Ion of Hollow Cobalt Ox Ide Nanoparticles by the Kirkendall Effect at Room Temperature at the Water-Air Interface", Nanoscale, 2013, 5, pp. 2429-2436, See abstract.

* cited by examiner

CARBON MATERIAL SUPPORTED HOLLOW METAL OXIDE NANOPARTICLES, METHODS AND APPLICATIONS

CROSS-REFERENCE TO RELATED APPLICATION

This application is related to, and derives priority from, U.S. Provisional Patent Application Ser. No. 61/816,436, filed 26 Apr. 2013 and titled Hollow Metal Oxide Materials, Methods and Applications, the contents of which is incorporated herein fully by reference. This application is also related to, and also derives priority from, Chinese Patent Application CN 103219510, filed 21 Mar. 2013 and titled Lithium Battery Negative Electrode Material Preparation Method and Its Product, the contents of which is also incorporated herein fully by reference.

STATEMENT REGARDING FEDERALLY SPONSORED RESEARCH AND DEVELOPMENT

This invention was made with government support under grants DE-FG02-87ER47298 and DE-SC0001086 awarded by the Department of Energy, and grant 1120296 awarded by the National Science Foundation. The government has certain rights in the invention.

BACKGROUND

Field of the Invention

Embodiments relate generally to hollow metal oxide nanoparticles, methods for preparation thereof and applications thereof. More particularly embodiments relate to structurally supported and functionally supported hollow metal oxide nanoparticles, methods for preparation thereof and applications thereof.

Description of the Related Art

Transition metal oxide (TMO) nanoparticle materials have attracted attention as lithium-ion battery (LIB) anode materials to replace the currently used graphite materials, in order to allow LIBs to achieve higher energy and power densities. Among candidate TMOs, cobalt oxide ($Co_3O_4$) is one of the most widely studied anode material candidates due to its high theoretical LIB capacity (890 $mAhg^{-1}$). A similarly high capacity is also found in iron oxide ($Fe_2O_3$, $Fe_3O_4$), manganese oxide ($MnO_2$) and nickel oxide (NiO) LIB anode material candidates.

Since improvements in LIB performance are likely to continue to be desirable, so also are novel and improved TMOs for use within LIBs, methods for fabrication of those improved TMOs for use within the LIBs and methods for use (i.e., applications) of those improved TMOs, including the LIBs.

SUMMARY

The embodiments provide a one-pot, two-step method to synthesize hollow transition metal oxide nanoparticles, such as but not limited to $Co_3O_4$ nanoparticles dispersed on and supported by a carbon material support, such as but not limited to an amorphous carbon material support. The synthesis or preparation of these carbon material supported hollow transition oxide nanoparticles may be accomplished via an all-solid-state method, producing the active hollow transition metal oxide nanoparticles on a carbon material support in one-pot on a lab bench, which can potentially be scalable to large quantities for industrial production. An impregnation-reduction method may be used for forming the hollow transition metal oxide nanoparticles dispersed on and supported by the carbon material support, followed by a thermal oxidation method. In general, the methodology in accordance with the embodiments first provides in a first process step an ionic impregnation of a suitable transition metal salt into a carbon material support carrier and reduction of the transition metal salt impregnated carbon material support carrier in a reducing atmosphere to form a carbon material supported transition metal particle (i.e., generally a nanoparticle). Then, in a second process step the method provides for an oxidation of the carbon material supported transition metal particle to provide a carbon material supported hollow transition metal oxide nanoparticle.

The embodiments also include a related materials composition in accordance with the embodiments, a related electrode in accordance with the embodiments and a related electrical component (i.e., such as but not limited to an electrochemical gas sensor, a supercapacitor or a battery (and in particular a LIB)) in accordance with the embodiments.

The embodiments contemplate that a nanoparticle in general has a dimension from about 1 to about 1000 nanometers.

Within the context of the embodiments use of the terminology "structurally supported hollow transition metal oxide nanoparticle" or "functionally supported hollow transition metal oxide nanoparticle" is intended to provide that an electrically active hollow transition metal oxide nanoparticle in accordance with the embodiments is supported physically (i.e., structurally) and with electrical continuity (i.e., functionally) upon a contiguous carbon material support and more particularly upon a contiguous nanostructured carbon material support.

Within the context of the embodiments the carbon material support may comprise a carbon material selected from the group including but not limited to amorphous carbon, crystalline carbon, graphitic carbon, graphene, graphene oxide, carbon nanotube and carbon microtube carbon material supports.

A hollow transition metal oxide nanoparticle in accordance with the embodiments that is supported by a carbon material support may be generally described by the formula $M_xO_y$, where: (1) M may include one or more transition metal elements selected from the group including but not limited to Co, Fe, Mn, Ni, Ti, Cu, Zn and V; (2) O is oxygen; (3) x may range from 1 to 3; and (4) y may range from 1 to 4.

A particular hollow transition metal oxide nanoparticle in accordance with the embodiments includes a transition metal oxide material in accordance with the foregoing chemical description, and also having: (1) a particle size from about 50 to about 300 nanometers; (2) a pore size from about 5 to about 100 nanometers (3) a hollow volume of from about 20 to about 60 percent.

The embodiments also contemplate that the hollow volume within a hollow transition metal oxide nanoparticle in accordance with the embodiments may include: (1) at least one major void of greater than about 50 nanometers; and (2) a plurality of minor voids of less than about 10 nanometers.

A particular method for preparing a material composition in accordance with the embodiments includes impregnating a carbon material support with a transition metal salt to form a transition metal salt impregnated carbon material support. The particular method also includes thermally annealing the transition metal salt impregnated carbon material support within a reducing environment to provide a reduced transition metal particle supported on the carbon material support. The particular method also includes thermally annealing the reduced transition metal particle supported on the carbon material support to provide a hollow transition metal oxide nanoparticle supported on the carbon material support.

A particular materials composition in accordance with the embodiments includes: (1) a carbon material support; and (2) a hollow transition metal oxide nanoparticle supported upon the carbon material support.

A particular electrode in accordance with the embodiments includes: (1) a conductive substrate; and (2) a coating located upon the conductive substrate and including a material composition comprising: (a) a carbon material support; and (b) a hollow transition metal oxide nanoparticle supported upon the carbon material support.

A particular electrical component in accordance with the embodiments includes an electrode comprising: (1) a conductive substrate; and (2) a coating located upon the conductive substrate and including a material composition comprising: (a) a carbon material support; and (b) a hollow transition metal oxide nanoparticle supported upon the carbon material support.

The particular electrical component in accordance with the embodiments may be selected from the group including but not limited to an electrochemical gas cell, a supercapacitor and a battery (i.e., such as but not limited to a LIB).

BRIEF DESCRIPTION OF THE DRAWINGS

The objects, features and advantages of the embodiments are understood within the context of the Detailed Description of the Non-Limiting Embodiments, as set forth below. The Detailed Description of the Non-Limiting Embodiments is understood within the context of the accompanying drawings, that form a material part of this disclosure, wherein:

FIG. 1 also shows XRD patterns of the Co/C and $Co_3O_4$/C nanoparticles.

DETAILED DESCRIPTION OF THE NON-LIMITING EMBODIMENTS

Figure 1:
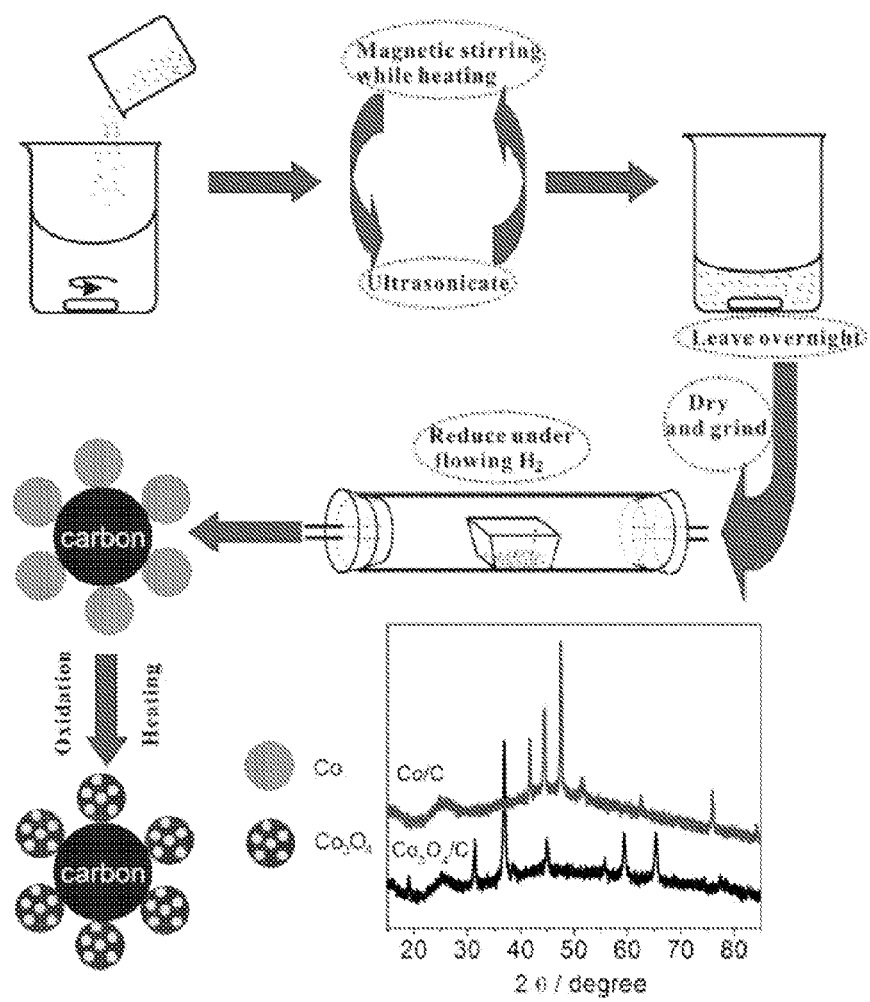
FIG. 1 shows a schematic illustration of s synthetic method for producing Co/C and hollow structured $Co_3O_4$/C nanoparticles.

The embodiments provide a one-pot, two-step method to synthesize hollow transition metal oxide nanoparticles (and in particular $Co_3O_4$ nanoparticles) dispersed on and supported by a carbon material support (such as but not limited to an amorphous carbon material support). The synthesis or preparation in accordance with the embodiments may be accomplished via an all-solid-state method, producing the active materials on a carbon support in one-pot on a lab bench, and can potentially be scalable to large quantities for industrial production. An impregnation-reduction method (i.e., $CoCl_2 \rightarrow Co$, for a cobalt transition metal) may be employed followed by an air-oxidation method (i.e., $Co \rightarrow Co_3O_4$, for the cobalt transition metal) to provide a carbon material supported active hollow transition metal oxide nanoparticle (i.e., and in particular an active hollow cobalt oxide transition metal oxide nanoparticle material) in accordance with the embodiments.

1. General Considerations for Forming Carbon Supported Hollow TMO Nanoparticles

Although the more specific considerations that follow describe the embodiments within the context of synthesizing carbon material supported $Co_3O_4$ hollow transition metal oxide nanoparticles in accordance with the embodiments, the embodiments are not intended to be so limited. Rather while using a synthesis or preparation methodology similar to the synthesis or preparation methodology used for forming the $Co_3O_4$ nanoparticles the embodiments also contemplate carbon supported hollow TMO nanoparticles including but not limited to cobaltosic oxide ($Co_3O_4$), cobalt monoxide (CoO), ferric oxide ($Fe_2O_3$), ferrous ferric oxide ($Fe_3O_4$), nickel monoxide (NiO), manganese dioxide ($MnO_2$), cupric oxide (CuO), cupric dioxide ($CuO_2$), zinc oxide (ZnO), vanadium dioxide ($VO_2$) carbon supported hollow TMO nanoparticles. The similar methodology is anticipated to include additional variants of an impregnation-reduction reaction followed by an oxidation reaction.

More generally, the embodiments also contemplate carbon supported hollow TMO nanoparticles derived from transitions metals including but not limited to cobalt, iron, nickel, manganese, titanium, copper, zinc and vanadium transition metals. The carbon material supported hollow transition metal oxide TMO nanoparticles may comprise stoichiometric or non-stoichiometric transition metal oxide materials in accordance with the foregoing list of transition metals.

A transition metal oxide that comprises a carbon material supported hollow transition metal oxide nanoparticle in accordance with the embodiments may be generally described by the formula $M_xO_y$, where: (1) M may include one or more transition metal elements selected from the group including but not limited to Co, Fe, Mn, Ni, Ti, Cu, Zn and V; (2) O is oxygen; (3) x may range from 1 to 3; and (4) y may range from 1 to 4. Due to the non-stoichiometric characteristics noted above, neither x nor y is limited to an integer.

In accordance with the embodiments, a carbon material support comprises a carbon material selected from the group including but not limited to amorphous carbon, crystalline carbon, graphitic carbon, graphene, graphene oxide, carbon nanotube and carbon microtube carbon material supports.

The embodiments in general provide a method that may be used for preparing as appropriate, at least one of a cathode and an anode within an electrical component including but not limited to an electrochemical gas sensor, a supercapacitor and a battery (i.e., in particular a LIB).

The embodiments are characterized within the context of a method that includes following steps:

(a) The method uses water, low-molecular weight alcohols (such as but not limited to methanol, ethanol, and isopropanol) or pure water mixture as a solvent, as well as a transition metal precursor within the context of at least one transition metal precursor salt that dissolves within the solvent. The transition metal precursor salt is selected from the group including but not limited to transition metal chlorides, nitrates, and sulfates having a general chemical structure of $ML_x$ where: (1) M is one or more of cobalt, iron, nickel, manganese, titanium, copper, zinc and vanadium; and (2) L is one or more of chloride, sulfate, nitrate, and x ranges from 1 to 4. Several illustrative but not limiting examples include $CoCl_2$, $FeCl_3$, $NiCl_2$, $MnCl_2$, $CuCl_2$, $ZnCl_2$, $VCl_2$, $Co(NO_3)_2$, $Fe(NO_3)_3$, $Mn(NO_3)_2$, $Ni(NO_3)_2$, $Cu(NO_3)_2$, $CoSO_4$, $FeSO_4$, $MnSO_4$, $NiSO_4$, $CuSO_4$, $ZnSO_4$, (i.e., simple anion salts of candidate transition metals) or a particular doping compound (i.e., mixed candidate transition metal salts). By mixing the transition metal precursor salt in the solvent, one obtains a transition metal precursor solution.

(b) One next adds a carbon material support to the resulting transition metal precursor solution, and processes (i.e., typically by ultrasonication and heating) the concentrated mixture until a pulpiness mixture (i.e., a slurry) is obtained. The slurry is characterized by a 4:1 to 1:4 mass ratio of carbon material support to transition metal ion material.

(c) One then further processes the resulting pulpiness mixture of step (b) by curing, drying and grinding. And one carries out still further processing of the cured, dried and ground pulpiness mixture in a chemical reaction (i.e., a reduction reaction) to thereby obtain a transition metal particle supported upon the carbon material support.

(d) One then further processes the resulting carbon material supported transition metal particles of step (c) with a thermal oxidative treatment and obtains a resulting carbon material supported hollow transition metal oxide nanoparticle, which may be used as a lithium-ion battery electrode material.

As further preferably, in step (a), the transition metal precursor may be a transition metal chloride, nitrate or sulfate.

As further preferably, in step (a), a concentration of the transition metal precursor may be controlled as 10 mg/mL to 100 mg/mL, and the low molecular weight alcohol may be selected from the group including but not limited to methyl alcohol, ethanol and propyl alcohol.

As further preferably, in step (b), by an ultrasonic dispersion with an alternate mode of thermal agitation, may be used to provide a concentrated slurry of appropriate characteristics for further handling.

As further preferably, in step (c), the pulpiness mixture may be treated at a temperature from about 40 to about 100 degrees Celsius to cure and dry the mixture, which is then ground into the powder form.

As further preferably, in step (c), the electronation (i.e., reduction) reaction may be undertaken in hydrogen atmosphere, and its reduction temperature range may be from about 300 to about 1000 degree Celsius, and a processing time may be from about 2 to about 10 hours.

As further preferably, in step (d), a heating temperature with respect to a thermal oxidative treatment is from about 250 to about 400 degree Celsius, and the heat-treatment time is from about 5 to about 20 hours.

As further preferably, the carbon material support in accordance with the embodiments may comprise a carbon material selected from the group including but not limited to amorphous carbon, crystalline carbon, graphitic carbon, graphene, graphene oxide, carbon nanotube and carbon microtube carbon material supports.

According to another aspect of the embodiments, a corresponding lithium cell electrode material product is also provided.

As further preferably, the lithium cell electrode material comprises the carbon material supported hollow transition metal nanoparticle material in accordance with the embodiments, wherein the transition metal oxide has a formula of $M_xO_y$ where: (1) M may be one or more elements selected from the group including but not limited to Co, Fe, Mn, Ni, Ti, Cu, Zn and V; (2) O is oxygen; (3) x may range from 1 to 3; and (4) y may range from 1 to 4. Several examples include but are not limited to $CO_3O_4$, CoO, $Fe_2O_3$, $Fe_3O_4$, NiO, $MnO_2$, CuO, $CuO_2$, ZnO, $VO_2$, $TiO_2$ or its the doping compound. As noted above the embodiments contemplate stoichiometric and non-stoichiometric compositions for any candidate transition metal oxide material. As well, a "doping compound" is intended as a hollow mixed metal oxide transition metal oxide that is also expected to be active in accordance with the embodiments.

As further preferably, the specific surface area of a rechargeable lithium-ion battery electrode material in accordance with the embodiments is from about 10 to about 100 $m^2/g$.

Within a method in accordance with the embodiments in general, and as a first process step, using water, alcohol or pure water mixture as the solvent, one selects a metal precursor $M_xL_y$, where: (1) M is a transition metal selected from the group including but not limited to Co, Fe, Ni, Mn, Ti, Cu, Zn, and V; and (2) L is the ligand counter-anion such as chloride, sulfate, nitrate, or carbonate. Several examples are $CoCl_2$, $FeCl_3$, $NiCl_2$, $MnCl_2$, $CuCl_2$, $ZnCl_2$, $VCl_2$, $Co(NO_3)_2$, $Fe(NO_3)_3$, $Mn(NO_3)_2$, $Ni(NO_3)_2$, $Cu(NO_3)_2$, $CoSO_4$, $FeSO_4$, $MnSO_4$, $NiSO_4$, $CuSO_4$, $ZnSO_4$, $FeCO_3$ or its the doping compound, for example metal chloride or nitrate etc. dissolve wherein a transition metal precursor solution is thereby obtained. Wherein, the concentration of the transition metal precursor is controlled as 10 mg/mL to 100 mg/mL, and the alcohol is selected from at least methyl alcohol, ethanol or the propyl alcohol.

Within the method in accordance with the embodiments one then adds a carbon material support that may be selected, for example, from the group including but not limited to amorphous carbon, crystalline carbon, graphitic carbon, graphene, graphene oxide, carbon nanotube and carbon microtube carbon material supports to the resulting transition metal precursor solution, wherein a mass ratio of transition metal ion to carbon support material is controlled to 4:1 to 1:4. One then concentrates the solution until a pulpiness slurry is obtained. Within the embodiments the foregoing concentration processing may result from ultra-sonic dispersion with an alternate mode of thermal treatment. The transition metal precursor and carbon material support dispersion is concentrated to form a pulpiness slurry to a point of ease of handling.

Within the method in accordance with the embodiments, the pulpiness slurry mixture that results is thermally treated from about 40 to about 100 degrees Celsius temperature condition and is cured, dried and ground. One, then carries out the electronation reduction reaction, to obtain a carbon material supported transition metal nanoparticle in accordance with the embodiments. The electronation reduction reaction is preferably undertaken in a hydrogen atmosphere, and its reduction temperature scope is from about 300 to about 1000 degree Celsius, and the thermal treatment time from about 2 to about 10 hours.

Finally, within the method in accordance with the embodiments, the carbon material supported transition metal particle is thermally annealed in an oxidizing environment, to provide a carbon material supported hollow transition metal oxide nanoparticle. The thermal oxidizing environment utilizes a temperature from about 250 to about 400 degree Celsius for a time period from about 5 to about 20 hours.

Additional and/or alternative parameters and/or limitations for a method in accordance with the embodiments are as follows.

Within the embodiments a carbon material support is impregnated with a transition metal salt in solution.

Within the embodiments the transition metal salt includes, but is not limited to a cobalt transition metal salt.

Within the embodiments the transition metal salt includes a transition metal selected from the group including but not limited to iron, manganese, nickel, titanium, copper, zinc and vanadium transition metals.

Within the embodiments the reducing environment is selected from the group including but not limited to: (1) a hydrogen gas and a mixture of hydrogen gas and up to about 90 percent inert gas such as nitrogen or argon; and (2) a liquid-based reducing reagent selected from the group including but not limited to sodium citrate, ascorbic acid, sodium borate hydrate, and hydrazine.

Within the embodiments a reducing temperature is from about 100° C. to about 800° C. and a reducing time is from about 1 hour to about 10 hours.

Within the embodiments, the oxidizing environment comprises at least one of: (1) an oxidizing gas selected from the group including but not limited to oxygen, air, and a mixture of oxygen with another inert gas; and (2) a liquid-based oxidizing reagent selected from the group including but not limited to hydrogen peroxide, and nitric acid.

Within the embodiments an oxidizing temperature is from about 100° C. to about 800° C., and an oxidizing time is from about 1 hour to about 10 hours.

Within the embodiments, a hollow transition metal oxide nanoparticle has: (1) a particle size from about 50 to about 300 nanometers; (2) a pore size from about 5 to about 100 nanometers; and (3) a hollow volume percentage from about 20 to about 60 percent. The hollow volume may include: (1) a single large void of greater than about 50 nanometers; and (2) a plurality of smaller void less than about 10 nanometers.

Figure 2:
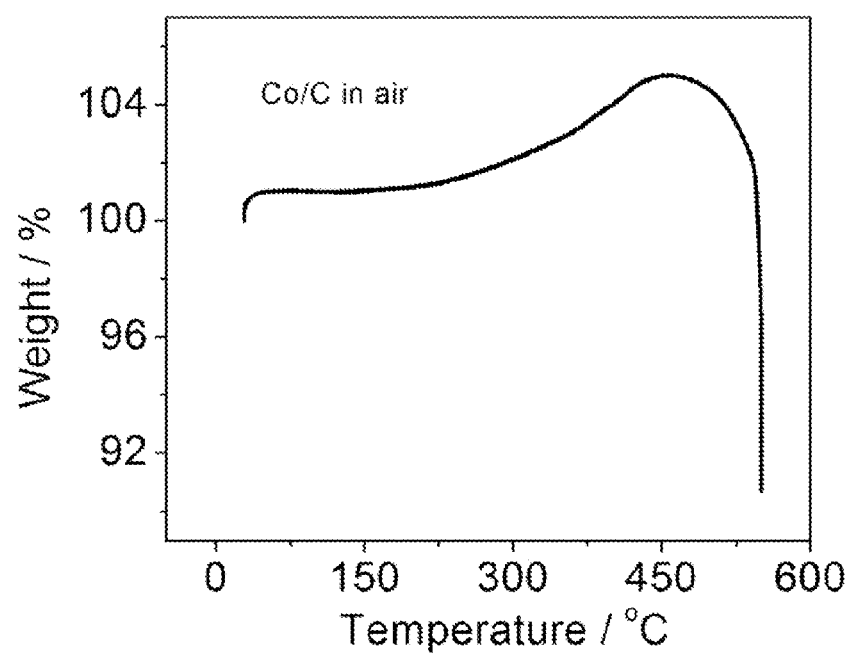
FIG. 2 shows a thermo gravimetric analysis (TGA) spectrum a of Co/C nanoparticle sample tested in flowing air. Two process took place. First, metallic Co nanoparticles were oxidized to $Co_3O_4$, showing the maximum increase of weight at about 460° C. Secondly, Vulcan XC-72 carbon support was oxidized starting at about 350° C. Therefore, in an effort to maximize the yield of $Co_3O_4$ and minimize the Vulcan XC-72 loss, an optimal heat-treatment temperature was chosen to be 400° C.

2. Specific Considerations for Forming Carbon Supported $Co_3O_4$ Hollow Sphere Nanoparticles As illustrated in FIG. 1, a $CoCl_2$ precursor material in accordance with the embodiments was first dispersed on the Vulcan XC-72 carbon support, and then reduced under flowing $H_2$ in a tube furnace at 300° C. After cooling to room temperature under a $N_2$ atmosphere, the metallic cobalt nanoparticles supported on carbon (Co/C) were collected. The as-prepared Co/C nanoparticles were then heat-treated in a tube furnace under open air at a ramp rate of 1° C./min up to 400° C. for 10 hours to form hollow structured $Co_3O_4$ nanoparticles (see more details in experimental section below). The voids were created during air-heating, as a result of the Kirkendall effect-the diffusion rates of cations and anions are not the same in the nanoparticle. A similar hollowing phenomenon can also be observed in other transition metal oxide materials following a formula of $M_xO_y$, where: (1) M may be one or more elements selected from the group including but not limited to Co, Fe, Mn, Ni, Ti, Cu, Zn and V: (2) O is oxygen; (3) x may range from 1 to 3; and (4) y may range from 1 to 4. An optimal heat-treatment temperature was chosen based on thermogravimetric analysis (TGA) of the Co/C in air as illustrated in FIG. 2. X-ray diffraction (XRD) shows, as illustrated in FIG. 1, a phase transformation from pure metallic Co to the spinel cobalt oxide phase ($Co_3O_4$). The diffraction peaks at $2\theta=41.7°$, $44.5°$, $47.5°$ can be indexed to the (100), (002), and (101) planes, respectively, corresponding to the hexagonal phase of Co (JCPDS: 05-0727). The XRD patterns of metallic Co show a dramatic transition after heat treatment under open air. The diffraction peaks at $2\theta=31.3°$, $36.9°$, $44.9°$, $59.4°$, $65.4°$ are indexed to (220), (311), (400), (511), and (440) planes respectively, matching with that of the cubic spinel $Co_3O_4$ (JCPDS: 42-1467). These results demonstrate the complete conversion of $CoCl_2$ to metallic Co, and then to $Co_3O_4$.

Figure 3:
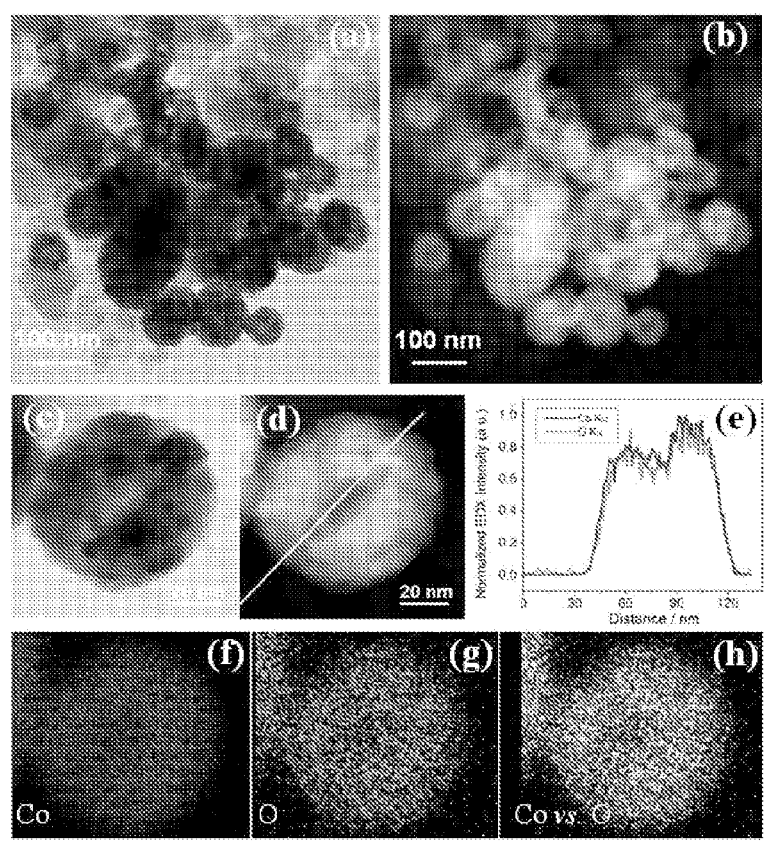
FIG. 3 shows microstructure analysis of an as-prepared hollow $Co_3O_4$/C nanoparticle sample. (a)-(b) HAADF and BF STEM of the overview images. (c)-(d) HAADF and BF STEM of a detailed nanoparticle, along with (e) EDX line profile of Co (red—darker curve) and O (green—lighter curve), showing the decrease of intensity of concentration in the middle. (f)-(g) EDX mapping of Co and O respectively and (h) overlay showing the homogeneity of the Co/O nanoparticle sample distribution.
Figure 4:
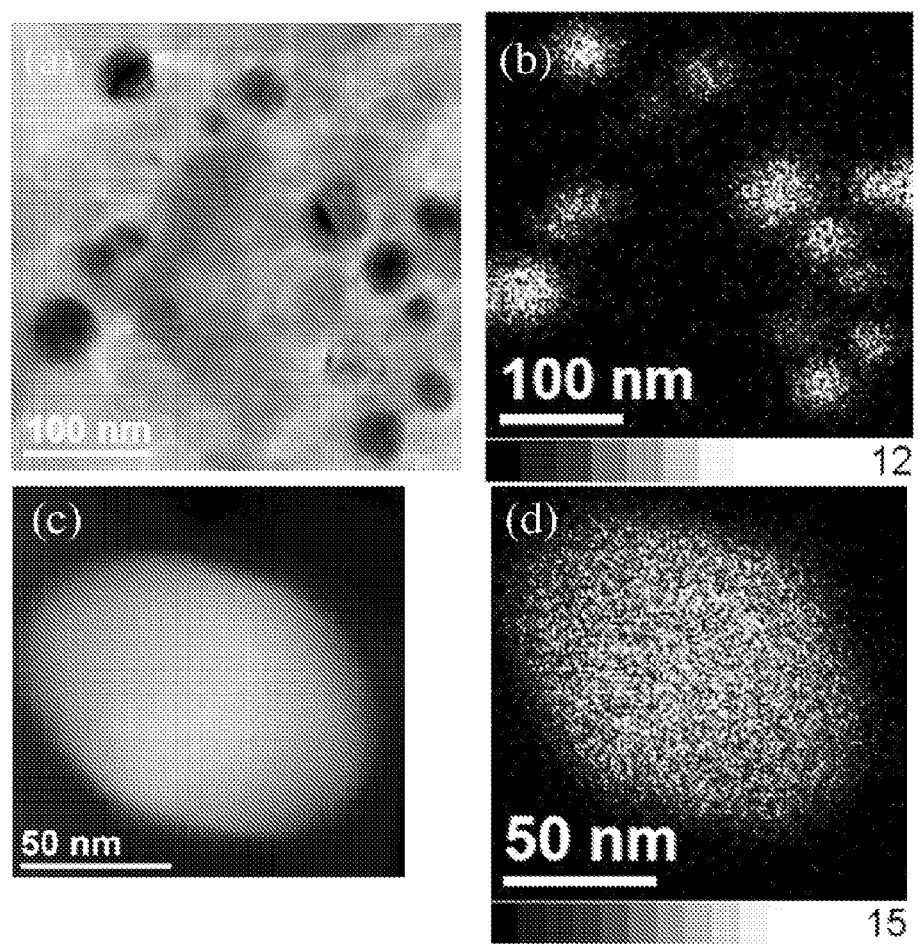
FIG. 4 shows analytic electron microscopy images of metallic Co/C. (a) BF-STEM overview and (b) EDX mapping of Co, followed by (c) HAADF-STEM image of a detailed Co/C nanoparticle with (d) EDX mapping of Co. The color scale bar used in (b) and (d) corresponds to the EDX intensity labeled on the images. These data show that Co/C had no hollow structure, while no noticeable oxide or chloride was detected by EDX.

To understand the microstructure of the as-synthesized hollow $Co_3O_4$/C material, one may perform high angle annular dark field and bright field scanning transmission electron microscopy (HAADF- and BF-STEM) imaging, shown in FIG. 3a and FIG. 3b. Typical nanoparticles had diameters ranging from 50 nm to 100 nm, with nanoparticle pore sizes ranging from 10 nm to 50 nm. All of the $Co_3O_4$ nanoparticles exhibited a hollow structure with a rough surface, in contrast to the metallic cobalt nanoparticles, which all showed a non-hollow structure, as illustrated in FIG. 4. A detailed view of one hollow nanoparticle is presented in FIG. 3c and FIG. 3d, with an oval-shaped pore shown clearly at the center, surrounded by multiple small vacancies. One may suspect that this 50 nm nanoparticle was formed by the coarsening of several smaller nanoparticles, each less than 10 nm in size, as illustrated in FIG. 3c. On the one hand, this large pore fraction greatly increases the surface-to-volume ratio, enabling more active material to participate in the electrochemical reaction. On the other hand, the interconnected structure should provide pathways for the diffusion of $Li^+$, facilitating charge transfer. The energy dispersive X-ray (EDX) line profile, as illustrated in FIG. 3e, shows that both the Co and O signals decrease in the middle in the void as expected. The EDX map, as shown in FIG. 3f, FIG. 3g and FIG. 3h show that the Co to O ratios are uniform across the particles, as expected for a single phase. Such a combination of pores and vacancies is desirable for superior electrochemical performance, since it not only shortens the diffusion distance for $Li^+$ and electrons, but also mitigates the volume expansion and the stresses during charge/discharge.

Figure 5:
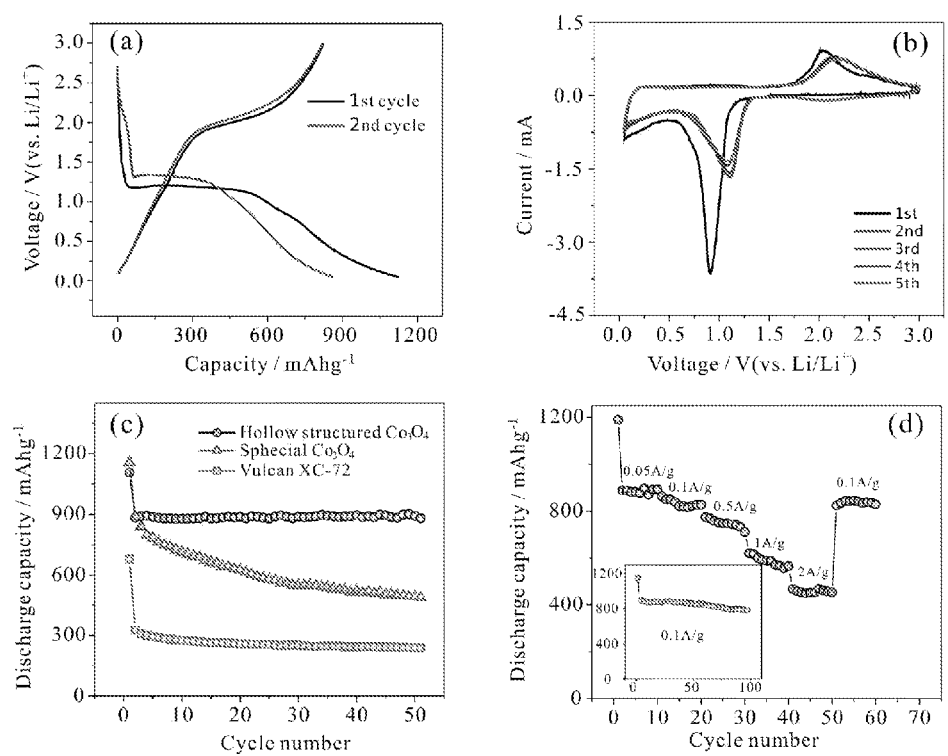
FIG. 5 shows electrochemical performance of hollow $Co_3O_4$/C. (a) Charge and discharge profiles of the $1^{st}$ and $2^{nd}$ cycles. (b) Cyclic voltammetry of the first 5 cycles (i.e., where first curve is separated from remaining four curves). (c) Comparison of discharge capacity of hollow structured $Co_3O_4$/C, special $Co_3O_4$/C and Vulcan XC-72. (d) Discharge capacity at various current densities. Note 50 mA/g is about 0.05 C (1 C is about 890 mA/g). The inset in (d) shows the cyclability of hollow structured $Co_3O_4$/C at a current of 100 mA/g, after 100 cycles.
Figure 6:
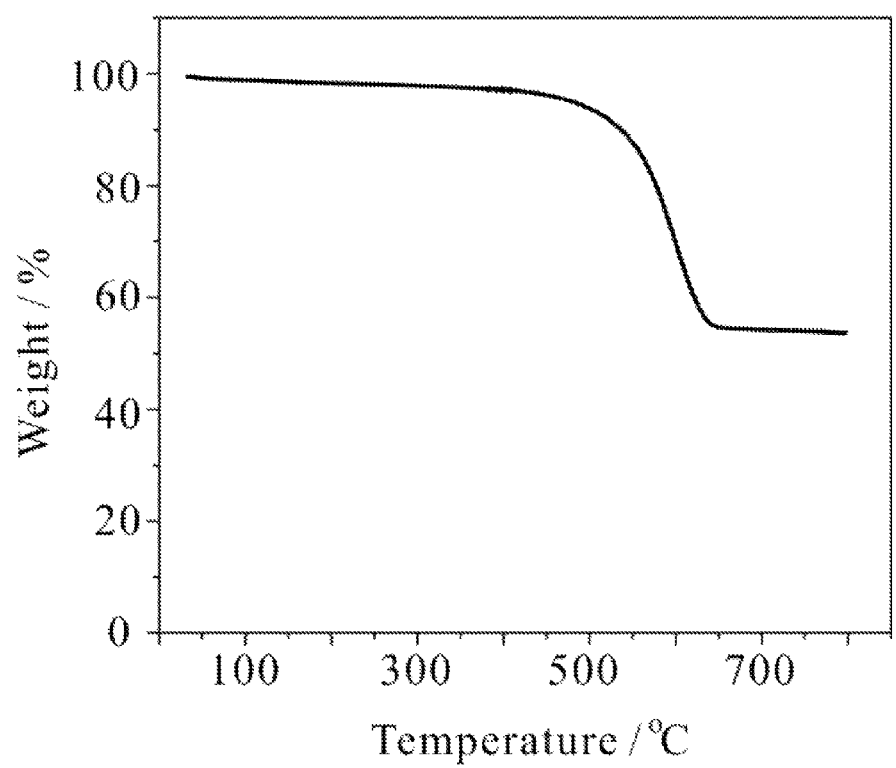
FIG. 6 shows TGA curve of $Co_3O_4$/C tested in flowing air to determine the mass loading of $Co_3O_4$. A plateau started to appear shortly after 600° C., indicating virtually a complete loss of Vulcan XC-72. The weight percentage of $Co_3O_4$ in the active LIB material was estimated to be 55%.

The electrochemical performance of the hollow $Co_3O_4$/C was performed in 2032 coin cells with Li foil as the counter electrode. FIG. 5a shows a typical discharge-charge profile of the hollow structured $Co_3O_4$ nanoparticles with a cutoff voltage of +0.05 V vs. Li at a current density of 50 mA/g. To accurately establish the capacity from only the active material $Co_3O_4$, and exclude the contribution from the carbon support material Vulcan XC-72, one may measure the loading of $Co_3O_4$ on carbon support via TGA, as illustrated in FIG. 6, and from the weight loss of carbon support, one may determine 55% $Co_3O_4$ loading by weight. In addition, one may calculate the capacity as a result of the addition of Vulcan XC-72, shown as the green plot of FIG. 3c. Using the following equation, one may determine the capacity derived only from $Co_3O_4$.

$$C_{Co_3O_4} = \frac{Q_{total} - C_C \times m_C}{m_{Co_3O_4}} \quad (1)$$

where $c_{Co_3O_4}$ the mass specific capacity of $Co_3O_4$ (the unknown), $Q_{total}$ is the measured coulomb charge, $m_{Co_3O_4}$ is the mass of $Co_3O_4$ (obtained from TGA, as illustrated in FIG. 6), $C_C$ is the mass specific capacity of the carbon support (obtained via a control experiment, as illustrated in FIG. 3c, the capacity of pure Vulcan XC-72), and $m_C$ is the mass of Vulcan XC72 (total material mass minus the mass of $Co_3O_4$). Equation (1) is robust when there is a carbon additive involved (for example, carbon black). As a comparison, without the correction of carbon support, one would observe a stabilized capacity of 1140 mAh/g, which is about 250 mAh/g higher than the theoretical capacity. It is thus believed that the capacity correction is necessary for anode material mixed with carbon upon discharged to lower voltage.

The voltage capacity profile in FIG. 5a shows a discharge plateau at about +1.1 V (vs. Li) for the $1^{st}$ cycle and about +1.2 V for the $2^{nd}$ cycle, with a high initial capacity of 1107 mAh/g, which dropped to 880 mAh/g after the $2^{nd}$ cycle. The irreversible capacity loss is frequently attributed to the decomposition of electrolytes and the formation of a solid-electrolyte interface (SEI) on the surface of the electrode materials, or an irreversible conversion process. FIG. 3b shows cyclic voltammograms (CV) of electrodes made from the hollow $Co_3O_4$ nanoparticles in a coin cell at a scan rate of 0.05 mV/s. The first cathodic scan exhibits an irreversible reduction peak at around +0.88 V, in good agreement with the irreversible capacity loss in FIG. 5a. After the $1^{st}$ scan, the cathodic peak shifts to about +1.2 V, and a corresponding anodic peak to about +2.1 V. Little changes were observed from the $2^{nd}$ cycle to the $5^{th}$ cycle, indicating good cycling stability. At a relatively low current density of 50 mA/g (1 C is about 890 mA/g), the reversible capacity of the hollow structured $Co_3O_4$ nanoparticles was around 880 mAh/g, as illustrated in FIG. 5c, which is very close to the theoretical capacity of 890 mAh/g. Such capacity is much higher than that of spherical $Co_3O_4$ nanoparticles (about 450 mAh/g after 50 cycles, as illustrated in FIG. 5c). Compared to a Li-intercalated Vulcan XC72 carbon support, as illustrated in FIG. 5c), the hollow $Co_3O_4$ exhibited about 3 times higher capacity. Reversible capacities of 850, 750, 600, and 450 mAh/g are observed after increasing the discharge/charge current density to 100, 500, 1000, and 2000 mA/g, respectively, as illustrated in FIG. 5d. Notably, after 50 cycles at varied current densities, the capacity could be restored to 880 mAh/g when the current density was reset to 50 mA/g. Furthermore, when the current density was increased to 100 mA/g, the discharge capacity can still be stabilized at about 770 mAh/g after 100 cycles, as shown in the inset of FIG. 53d. These data demonstrate it as a promising candidate for anode material for LIBs.

Figure 7:
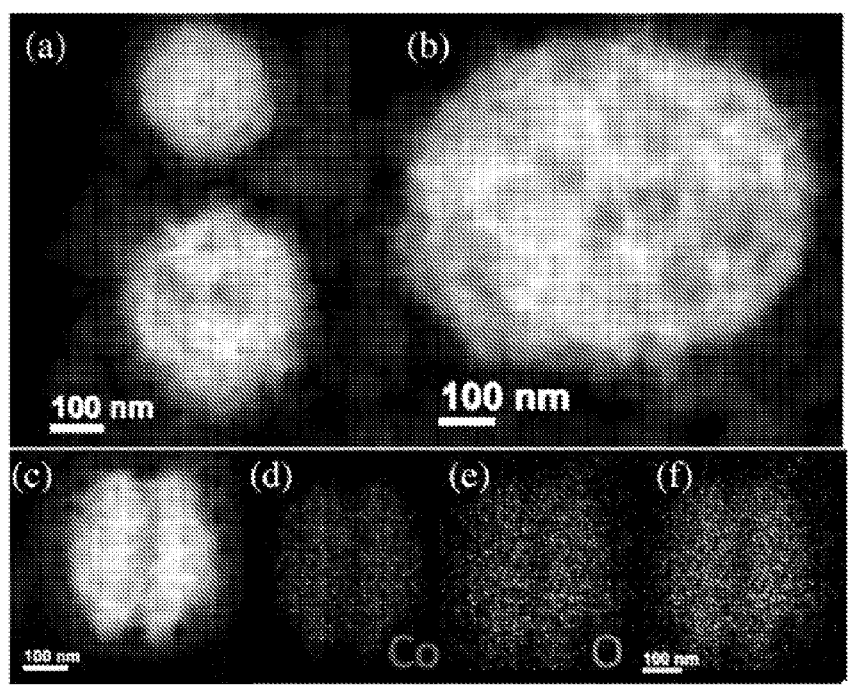
FIG. 7 shows a microstructure of $Co_3O_4$/C after 50 cycles at a rate of 50 mA/g. (a)-(c) HAADF-STEM images of several nanoparticles. Compared with the as-prepared material, the diameter has increased 5-8 fold, likely due to coarsening events during the electrochemical cycling. However, the hollow structure is still preserved, as evidenced by (d)-(f) EDX mapping of Co and O and its overlay, revealing that the nanoparticle is still homogenous.

The structural stability of the hollow structures was verified by disassembling the coin-cell and imaging the $Co_3O_4$/C structure after 50 cycles at 50 mA/g. FIG. 4a, FIG. 4b and FIG. 4c show the HAADF-STEM images of several aged composite nanoparticles. In comparison to the as-prepared sample, the diameter has increased by a factor of 5-8, likely due to the coarsening events happened during the electrochemical reaction. However, the hollow structure was maintained even after the intensive battery operation. The EDX mapping, as illustrated in FIG. 7d, FIG. 7e and FIG. 7f, also confirms that Co and O still were homogenously distributed within the nanoparticle. One may attribute the cycling stability of hollow $Co_3O_4$/C to its robust structure. In spite of the volume expansion, the battery can still maintain stable performance during $Li^+$ intercalation and deintercalation.

In conclusion, a method of preparing hollow $Co_3O_4$/C nanoparticles has been developed by a very simple two-step solid state synthesis process. During LIBs testing, the hollow $Co_3O_4$ exhibited excellent discharge capacity and durable performance when compared to non-hollow structures, likely due to the void spaces inside the particles, as illustrated in FIG. 5c. Due to the nature of solid-state synthesis, this method represents a simple and cost-effective way for manufacturing hollow TMO nanoparticles and thus represents a promising future in large-scale LIB materials production. Further studies are ongoing, to establish the relationship between the air flow rate and nanoparticle size distribution, the correlation between heating temperature and battery performance, the role of different transition metal precursors, and others. By optimizing these parameters, we believe that this facile synthetic method can be useful for large-scale LIB anode manufacture.

3. Experimental Details 3.1 Material Synthesis

The hollow $Co_3O_4$/C material was synthesized via an impregnation-reduction method followed by an air-oxidation procedure. Namely, 1.61 g of $CoCl_2.6H_2O$ were dissolved in ultrapure water, with 0.6 g of Vulcan XC72® added to the solution, which was ultrasonicated for 30 mins to achieve homogeneity. A thick carbon slurry was obtained by repeated concentration using heat stirring and dispersion using sonication. After heated at 60° C. for about 12 hours under a vacuum oven, the dried sample was grinded and placed in a ceramic heating boat, and transferred to a tube furnace. Under forming gas (about 5% hydrogen in nitrogen) flow, $CoCl_2/C$ was reduced to Co/C at 300° C. for 5 hours. The Co/C nanoparticles, with 40 wt % of Co metal, were then obtained by cooling the precursor to room temperature under a nitrogen atmosphere. The Co/C nanoparticles were placed into the tube furnace again and heated to 400° C. at a heating rate of 1° C./min in air atmosphere. The nanoparticles were incubated at 400° C. for 10 hours to obtain the hollow $Co_3O_4$ on the carbon support.

3.2 Material Characterization

Powder X-ray diffraction (XRD) was performed by using a Rigaku® Ultima VI diffractometer, and diffraction patterns were collected at a scanning rate of 5°/min and with a step of 0.02°. Electron microscopy imaging was carried out using a Schottky-field-emission-gun Tecnai F20 scanning transmission electron microscope (STEM) operated at 200 keV. A high-angle annular dark field detector provided an incoherent projection image of the specimen with a signal intensity proportional to the amount of material and its atomic number, which is also known as Z-contrast. The energy dispersive x-ray (EDX) analysis was performed in F20 using an Oxford detector, at a beam current of about 1 nA. An EDX resolution of 1-5 nm is routinely achieved on this setup. The material was stable under prolonged exposure to the electron beam (about 10-20 mins), which was verified by comparing HAADF-STEM images before and after EDX acquisition.

3.3 Electrochemical Measurement

Electrochemical measurements were carried out in CR 2032 coin cells assembled in an argon-filled glove box with lithium metal as the anode. The anodes consisted of 90 wt % active materials and 10 wt % polytetrafluoroethylene (PTFE) as a binder, which were rolled into a thin film. After drying under vacuum at 40° C., the film was cut into circular electrodes with an area of 0.71 cm². The cut film was pressed onto nickel foam as one electrode. The counter electrode was Li metal. The two electrodes were separated by a polymeric material (Celgard 2320). The electrolyte was 1.0 M $LiPF_6$ in a 1:1 ratio of EC (Ethylene carbonate):DEC (Diethylene carbonate). Galvanostatic charge/discharge of the coin cells were carried out at room temperature using an Arbin battery testing system with a constant discharge/charge current density varying from 0.05 to 2 A/g and a voltage range of +0.05-+3.0 V at room temperature. Cyclic voltammetry (CV) testing of the cells was performed on a Solartron electrochemistry working station at a scan rate 0.05 mV/s. All the capacities were normalized to the mass of the $Co_3O_4$ in the active material. To exclude the capacity of Vulcan-XC 72 in the measurement, a control experiment with only Vulcan XC-72 was carried out, and the actual capacity from $Co_3O_4$ is calculated based on the following equations.

$$Q_{total} = C_{Co_3O_4} \times m_{Co_3O_4} + C_C \times m_C \quad (1)$$

Where $Q_{total}$ is the measured coulomb charge, $C_{Co_3O_4}$ is the mass specific capacity of $Co_3O_4$, $m_{Co_3O_4}$ is the mass of $Co_3O_4$, $C_C$ is the mass specific capacity of carbon support, $m_C$ is the mass of carbon support.

4. Additional Embodiments 4.1 Example 1

1.61 g of $CoCl_2$ $6H_2O$ was dissolved in 50 mL ultrapure water. 0.6 g of Vulcan XC72® was added into the solution above. The solution was ultrasonicated to achieve homogeneity. A non-liquid carbon slurry was obtained by repeated concentration using heat stirring and dissipation using sonication. The slurry was incubated for 12 hours. The solution was heat dried in the oven under 60° C. The heat dried precursor was placed into the ceramic tube in the tube furnace, and was further reduced in forming gas (about 5% hydrogen in nitrogen) atmosphere under 350° C. for 5 hours. The Co/C nanoparticles with 40 wt % of Co metal were then obtained by cooling the precursor to room temperature. The Co/C nanoparticles were placed into the tube furnace and heated to 400° C. with the rate of 1° C./min in air atmosphere. The nanoparticles incubated under 400° C. for 10 hours to obtain the mesoporous $Co_3O_4$ on the carbon support.

4.2 Example 2

0.8 g of $CoCl_2$ $6H_2O$ was dissolved in 50 mL methanol. 08 g of carbon black was added into the solution above. The solution was ultrasonicated to achieve homogeneity. A non-liquid carbon slurry was obtained by repeated concentration using heat stirring and dissipation using sonication. The slurry was incubated for 12 hours. The solution was heat dried in the oven under 50° C. The heat dried precursor was placed into the ceramic tube in the tube furnace, and was further reduced in forming gas atmosphere under 300° C. for 5 hours. The Co/C nanoparticles with 20 wt % of Co metal were then obtained by cooling the precursor to room temperature. The Co/C nanoparticles were placed into the tube furnace and heated to 350° C. with the rate of 1° C./min in air atmosphere. The nanoparticles incubated under 400° C. for 10 hours to obtain the mesoporous $Co_3O_4$ on the carbon support.

4.3 Example 3

3.22 g of $CoCl_2$ $6H_2O$ was dissolved in 50 mL ethanol. 0.2 g of mesoporous carbon was added into the solution above. The solution was ultrasonicated to achieve homogeneity. A non-liquid carbon slurry was obtained by repeated concentration using heat stirring and dissipation using sonication. The slurry was incubated for 12 hours. The solution was heat dried in the oven under 40° C. The heat dried precursor was placed into the ceramic tube in the tube furnace, and was further reduced in forming gas atmosphere under 400° C. for 5 hours. The Co/C nanoparticles with 80 wt % of Co metal were then obtained by cooling the precursor to room temperature. The Co/C nanoparticles were placed into the tube furnace and heated to 350° C. with the rate of 1° C./min in air atmosphere. The nanoparticles incubated under 350° C. for 15 hours to obtain the mesoporous $Co_3O_4$ on the carbon support.

4.4 Example 4

2.14 g of $FeCl_2$ $6H_2O$ was dissolved in 50 mL propanol. 0.4 g of carbon black was added into the solution above. The solution was ultrasonicated to achieve homogeneity. A non-liquid carbon slurry was obtained by repeated concentration using heat stirring and dissipation using sonication. The slurry was incubated for 12 hours. The solution was heat dried in the oven under 60° C. The heat dried precursor was placed into the ceramic tube in the tube furnace, and was further reduced in forming gas atmosphere under 300° C. for 10 hours. The Fe/C nanoparticles with 60 wt % of Fe metal were then obtained by cooling the precursor to room temperature. The Fe/C nanoparticles were placed into the tube furnace and heated to 350° C. with the rate of 1° C./min in air atmosphere. The nanoparticles incubated under 350° C. for 10 hours to obtain the mesoporous $Fe_3O_4$ on the carbon support.

4.5 Example 5

3.24 g of $NiCl_2$ $6H_2O$ was dissolved in 50 mL water. 0.2 g of graphene oxide was added into the solution above. The solution was ultrasonicated to achieve homogeneity. A non-liquid carbon slurry was obtained by repeated concentration using heat stirring and dissipation using sonication. The slurry was incubated for 12 hours. The solution was heat dried in the oven under 40° C. The heat dried precursor was placed into the ceramic tube in the tube furnace, and was further reduced in forming gas atmosphere under 400° C. for 5 hours. The Ni/C nanoparticles with 80 wt % of Ni metal were then obtained by cooling the precursor to room temperature. The Ni/C nanoparticles were placed into the tube furnace and heated to 250° C. with the rate of 1° C./min in air atmosphere. The nanoparticles incubated under 250° C. for 10 hours to obtain the mesoporous NiO on the carbon support.

4.6 Example 6

5.71 g of $Fe(NO_3)_3$ $9H_2O$ was dissolved in 50 mL water. 0.2 g of graphene was added into the solution above. The solution was ultrasonicated to achieve homogeneity. A non-liquid carbon slurry was obtained by repeated concentration using heat stirring and dissipation using sonication. The slurry was incubated for 12 hours. The solution was heat dried in the oven under 100° C. The heat dried precursor was placed into the ceramic tube in the tube furnace, and was further reduced in forming gas atmosphere under 1000° C. for 2 hours. The Fe/C nanoparticles with 80 wt % of Co metal were then obtained by cooling the precursor to room temperature. The Fe/C nanoparticles were placed into the tube furnace and heated to 250° C. with the rate of 1° C./min in air atmosphere. The nanoparticles incubated under 250° C. for 20 hours to obtain the mesoporous $Fe_3O_4$ on the carbon support. Use example 1, we illustrate the characterization of the performance of the material produced in this invention. The other examples show similar results as compared to this one.

5. Performance within a Lithium Ion Battery Electrode

Figure 8:
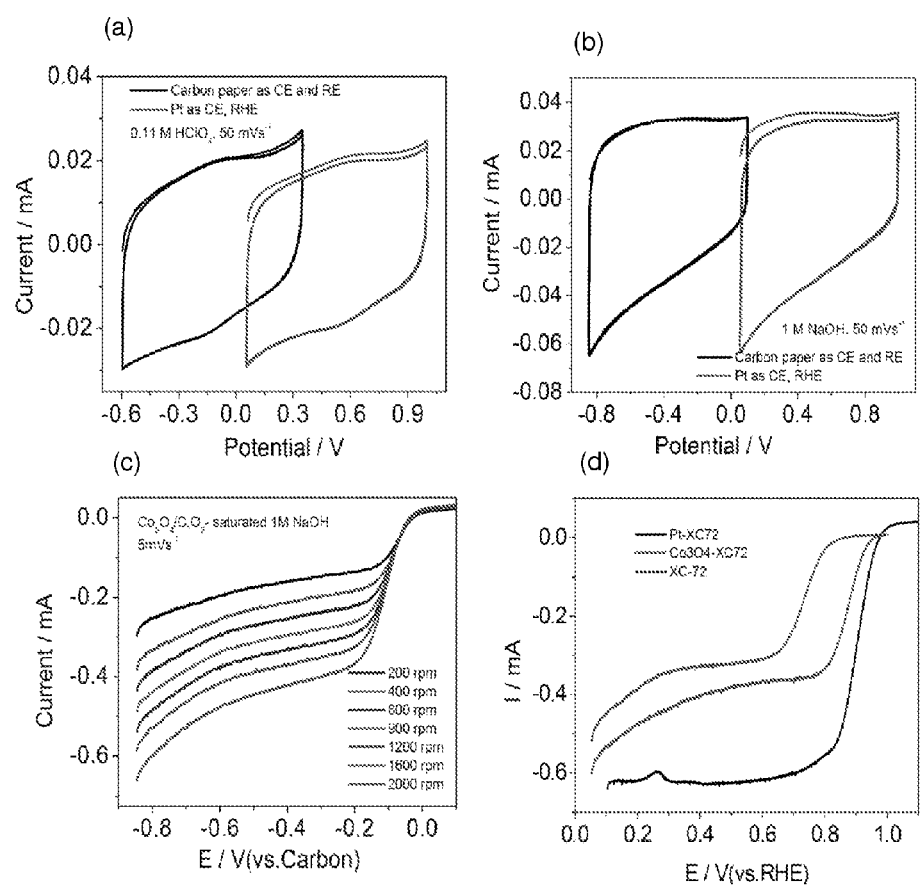
FIG. 8 shows electrochemical performance toward fuel cell catalysis. (a) Cyclic voltammograms of as-prepared $Co_3O_4$ catalysts in perchloric acid with comparisons with platinum; (b) Cyclic voltammograms of as-prepared $Co_3O_4$ catalysts in sodium hydroxide with comparisons with platinum; (c) Oxygen reduction reaction of $Co_3O_4$ catalysts in saturated 1M NaOH with scan rate of 5 mV/s (data curves in same order as legend); (d) Comparison of oxygen reduction reaction of Pt and carbon XC-72 support at a rotation rate of 1600 rpm (data curves in inverted order with respect to legend).

FIG. 8 shows electrochemical performance characteristics of an electrode formed using a $Co_3O_4$ nanoparticle in accordance with the embodiments. The electrode was formed with 90% (by weight) Co3O4 as active materials, 5% conductive Super-P carbon, and 5% polyvinylidene fluoride (PVDF) as binder.

FIG. 8 shows electrochemical performance toward fuel cell catalysis. (a) Cyclic voltammograms of as-prepared $Co_3O$ catalysts in perchloric acid with comparisons with platinum; (b) Cyclic voltammograms of as-prepared $Co_3O_4$ catalysts in sodium hydroxide with comparisons with platinum; (c) Oxygen reduction reaction of $Co_3O_4$ catalysts in saturated 1M NaOH with scan rate of 5 mV/s; (d) Comparison of oxygen reduction reaction of Pt and carbon XC-72 support at a rotation rate of 1600 rpm.

All references, including publications, patent applications, and patents cited herein are hereby incorporated by reference in their entireties to the extent allowed, and as if each reference was individually and specifically indicated to be incorporated by reference and was set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein is merely intended to serve as a shorthand method of referring individually to each separate value falling within the range, unless otherwise indicated herein, and each separate value is incorporated into the specification as if it was individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A method for preparing a material composition comprising:
    impregnating a carbon material support with a transition metal salt to form a transition metal salt impregnated carbon material support;
    thermally annealing the transition metal salt impregnated carbon material support within a reducing environment to provide a reduced transition metal particle supported on the carbon material support; and
    thermally annealing the reduced transition metal particle supported on the carbon material support within an oxidizing environment to provide a hollow transition metal oxide nanoparticle supported on the carbon material support, wherein:
    the hollow transition metal oxide nanoparticle has:
    a particle size from about 50 to about 300 nanometers;
    a pore size from about 5 to about 100 nanometers; and
    a hollow volume percentage from about 20 to about 60 percent, wherein the hollow volume includes:
        a primary void of greater than about 50 nm;
        a plurality of secondary voids of less than about 10 nm; and
        a uniform elemental distribution of metal and oxygen across the nanoparticle.

* * * * *